United States Patent
Ardizzone

[11] Patent Number: 4,626,239
[45] Date of Patent: Dec. 2, 1986

[54] COLONIC LAVAGING MACHINE

[76] Inventor: Nicholas Ardizzone, 102 E. Eight St., Vidalia, Ga. 30474

[21] Appl. No.: 782,043

[22] Filed: Sep. 30, 1985

[51] Int. Cl.⁴ .................. A61M 7/00; A61B 10/00
[52] U.S. Cl. ................................. 604/31; 604/83;
                                              604/118; 128/750
[58] Field of Search .......................... 604/27-35,
                                       604/82-85, 118, 244; 128/750

[56] References Cited
U.S. PATENT DOCUMENTS

| | | | |
|---|---|---|---|
| 2,024,967 | 12/1935 | Dierker | 604/30 X |
| 3,044,465 | 7/1962 | Anderson et al. | 604/83 |
| 3,570,488 | 3/1971 | Diskin et al. | 604/31 |
| 4,190,059 | 2/1980 | Holt | 128/750 |

Primary Examiner—Dalton L. Truluck
Attorney, Agent, or Firm—Robert B. Kennedy

[57] ABSTRACT

A colonic lavaging machine has a pressure switch operable by pressure in a water supply line to a speculum. The pressure switch is coupled with a valve that cyclically controls the flow of waste water from the speculum.

6 Claims, 2 Drawing Figures

COLONIC LAVAGING MACHINE

TECHNICAL FIELD

This invention relates to methods and apparatuses for lavaging the colon.

BACKGROUND OF THE INVENTION

Medical devices have been employed in colonic therapy for many years. For example, in 1935 U.S. Pat. No. 2,024,967 was issued for apparatus for rehabiliting peristalsis of the colon. This device included means for inducing water into the colon and for varying the pressure of the water so as to cause the colon to expand and contract as a technique in dislodging fecal material from the colon. Other apparatuses have since then been developed to provide improved means for controlling the temperature and pressure of the water injected into the colon. Exemplary of such improved methods and apparatuses are those disclosed in U.S. Pat. Nos. 2,832,341, 3,044,465, 3,678,932, 3,823,741 and 4,190,059. Thus today colonic machines for irrigating and lavaging the lower intestines have reached a relatively high degree of refinement.

Modern colonic machines are normally used by therapists in the following manner. A speculum that is secured to flexible hosing which extends from the machine, is inserted into the anal canal by the attendant and a supply of warm water injected via the speculum into the colon at a low pressure. While the therapist massages the patient's abdomen he observes the pressure of the water within the speculum and patient from a gauge. As the water fills the colon pressure increases. Once the pressure reaches a selected upper level, such as one pound, above which the patient would experience discomfort, the therapist operates a valve in a drain line that extends from the speculum whereupon the pressure decreases as waste water exits the colon. While drainage occurs the flow of fecal material and water is observed through a sight or view tube so that the therapist may observe the matter being discharged for diagnostic purposes. Once the pressure has dropped substantially, such as to one quarter pound, the drain valve is closed and the operative cycle repeated until the colon has been well cleansed.

Though the just described machine and procedure has proved quite effective in colonic therapy, it has been beset by an adverse inconsistency that arises from the fact that the therapist must constantly monitor water pressure over a protracted period of time, such as 20 minutes. In the event the attendant or therapist engages in conversation with the patient or becomes otherwise distracted, he or she may fail to observe that the pressure has increased beyond the upper limit. In this case the patient will normally experience discomfort or even pain. A potential for damage to the intestines will also arise. Even where the attendant properly monitors and operates the drain valve such operation inherently requires momentary suspensions of the massaging activities and continual relocation of the attendant's hands between the patient and machine. The present invention therefore is directed at alleviating these just described problems and limitations associated with colonic lavaging machines of the prior art.

SUMMARY OF THE INVENTION

In one form of the invention apparatus for lavaging the colon comprises a speculum for insertion into the anal canal of a patient for lavaging the colon and extracting matter lodged therein. The apparatus includes a water supply line connected with the speculum and sensing means for sensing the pressure of water in the water supply line. The apparatus further includes a drain line connected with the speculum and valve means coupled with the sensing means for controlling the flow of water through the drain line in response to the pressure of water in the water supply line sensed by the sensing means.

In another form of the invention a colonic lavaging machines comprises a housing, a water supply conduit mounted within the housing through which water may be fed from a water supply to a speculum and a water drain conduit mounted within the housing through which waste water may be drained from the speculum. The machine also has means for sensing the pressure of water in the water supply conduit and means coupled with the sensing means for controlling the flow of waste water in the water drain conduit responsive to the pressure of water sensed by the sensing means in the water supply conduit.

In yet another form of the invention apparatus for lavaging the colon comprises a speculum for insertion into the anal canal of a patient for lavaging the colon and extracting matter lodged therein. The apparatus has conduit means for feeding fresh water to the speculum and for draining waste water from the speculum. The apparatus further includes means for automatically cycling the pressure of water in the speculum between preselected upper and lower limits.

DETAILED DESCRIPTION

Figure 1:
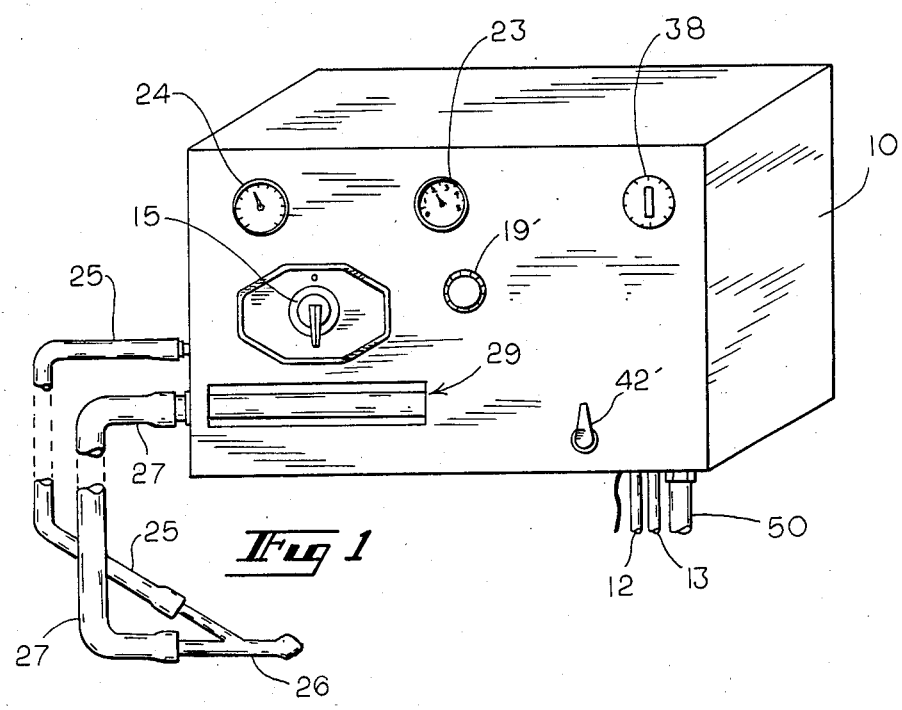
FIG. 1 is a perspective front view of a colonic lavaging machine that embodies principles of the present invention.
Figure 2:
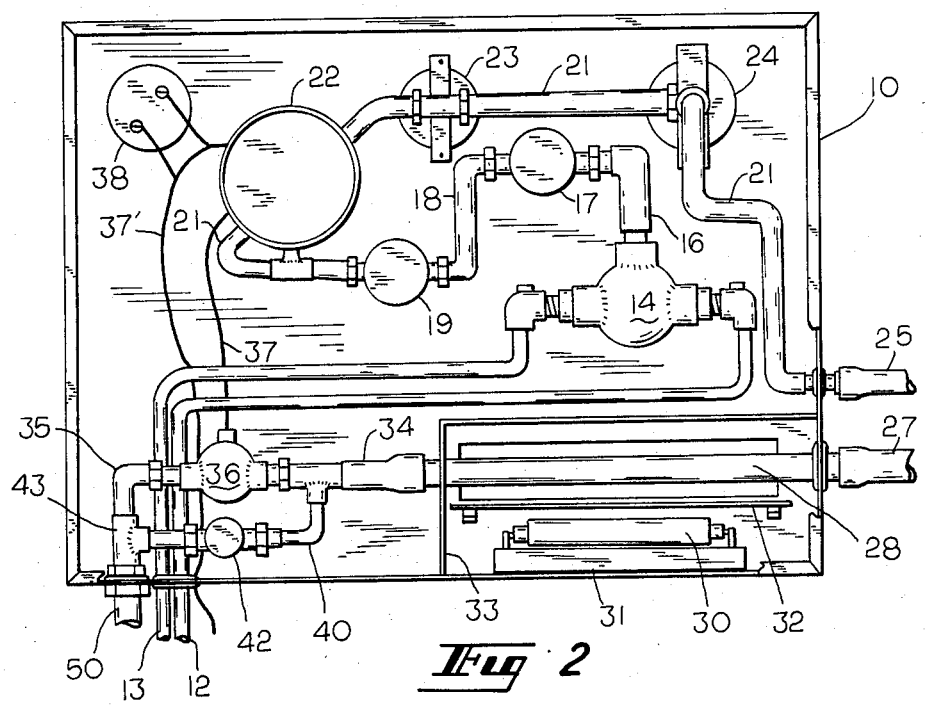
FIG. 2 is a rear elevational view of the machine shown in FIG. 1 with its back housing panel removed to reveal internal components.

With reference next to the drawing, there is shown a colonic lavaging machine having a housing 10 through the bottom of which extend a hot water supply conduit or line 12 and a cold water supply line 13 to a thermostatically controlled mixing valve 14 mounted within the housing that may be manually set by rotation of a lever 15 on the front of the housing. A conduit 16 extends from the mixing valve to a pressure regulator 17 which reduces the municipal water line pressure of some 40 to 60 pounds per square inch to four pounds. Another conduit 18 extends from the pressure regulator to a pressure valve 19 that is manually controlled by a valve knob 19' located exteriorly of the front of the housing 10 which serves to reduce the water pressure further. Another conduit 21 extends from the pressure valve 19 past a pressure switch 22, past a pressure gauge 23 and a temperature gauge 24 and out of a side of the housing to an exterior, flexible conduit 25. The exterior conduit 25 extends to a speculum 26. Another exterior, flexible conduit 27 provides a drain or return line from the speculum to a transparent view tube 28 located behind a slot 29 formed in the front of the housing. A lamp 30, controlled by a ballast 31, is mounted within the housing beneath a light diffuser 32 for illuminating the view tube beneath a light baffle 33. The view tube passes through an opening in the baffle to a T-joint 34.

A drain line 35 extends from the T-joint through a solenoid actuatable diaphragm type valve 36, which is electrically connected by electrical conductor lines 37 to the pressure switch 22 and to an optional electrical timer 38. The drain tube extends out of the bottom of the housing to an unshown waste collection site. An auxiliary conduit 40 also extends from the T-joint 34 through an optional ball valve 42, manually operatable by a valve handle 42', to juncture with the drain line 35 at another T-joint 43. Another electrical conductor line 37' extends out of the bottom of the housing to a source of municipal power for operation of the solenoid valve 36 via pressure switch 22 and for providing power to the timer 38.

In preparing to use the machine the valve 42 is closed, the hot and cold water lines 12 and 13 are connected to respective supply lines, and the desired temperature obtained by adjusting the thermostatic control mixing valve 14. Once the proper temperature is observed on the temperature gauge 24 the pressure may be adjusted as by simply elevating the speculum 26 until the pressure on the pressure gauge 23 reads one quarter pound. As the pressure switch 22 has been preset to operate on the high end at one pound and at the low end at one quarter pound, the machine is now ready for use.

To lavage the colon the speculum is inserted into the anal cavity whereupon warm water is fed at low pressure into the large intestine or colon until it reaches an area blocked by fecal matter. As this is done the pressure switch, having senses a low limit pressure of one quarter pound, has caused valve 36 to close the drain line. Thus, once water has filled the view tube and encountered an area of blockage in the colon, it causes the colon to expand until a pressure of one pound is reached. Once the pressure reaches this level the electrical pressure switch 22 activates the solenoid operable diaphragm valve 36 causing it to open whereupon waste water is drained out of the system through the drain line 50. As this occurs the flow of fecal material out of the patient may be observed as it passes through the view tube. Once the pressure has decreased to a quarter pound the pressure sensitive switch 22 again operates so as to activate the solenoid diaphragm valve 36 whereupon the drain line is reclosed and water again starts to fill the colon. This oscillation of the water pressure thus accompanies the repeated filling and evacuation of the colon with water as fecal material is removed and usually the therapist massages the patient's abdomen. At the conclusion of the treatment the speculum is removed from the patient and the system flushed clean.

It thus is seen that a colonic lavaging machine is now provided which overcomes problems associated with those of the prior art. It should be understood, however, that the just described embodiment merely illustrates principles of the invention in one preferred form. Many modifications, additions and deletions may, of course, be made thereto without departure from the spirit and scope of the invention as set forth in the following claims.

I claim:
1. Apparatus for lavaging the colon comprising:
   a speculum for insertion into the anal canal of a patient for lavaging the colon and extracting matter lodged therein;
   a water supply line connected with said speculum;
   sensing means for detecting a preselected high level of water pressure in said water supply line and for detecting a preselected low level of water pressure in said water supply line;
   a drain line connected with said speculum; and
   valve means coupled with said sensing means for controlling the flow of water through said drain line by increasing drain flow rate upon said sensing means detecting said high level and by decreasing drain flow rate upon said sensing means detecting said low level.

2. The apparatus of claim 1 wherein said pressure sensing means comprises a pressure operable switch.

3. The apparatus of claim 2 wherein said valve means comprises a solenoid actuatable diaphragm valve electrically connected with said pressure operable switch.

4. A colonic lavaging machine comprising a housing; a water supply conduit mounted within said housing through which water may be fed from a water supply to a speculum; a water drain conduit mounted within said housing through which waste water may be drained from the speculum; means for sensing the pressure of water in said water supply conduit; and means coupled with said sensing means for controlling the flow of waste water in said water drain conduit responsive to a high and to a low level of water pressure sensed by said sensing means in said water supply conduit, said control means including an electrical pressure switch operatively associated with said water supply conduit, a solenoid valve operatively associated with said water drain conduit, and electrical conductor means coupling said solenoid valve with said pressure switch.

5. Apparatus for lavaging the colon comprising a speculum for insertion into the anal canal of a patient for lavaging the colon and extracting matter lodged therein; conduit means for feeding fresh water to said speculum and for draining waste water from said speculum; and means for automatically cycling the pressure of water in said speculum between preselected upper and lower limits.

6. The apparatus of claim 5 wherein said automated cycling means includes means for sensing the pressure of water in said conduit means and valve means coupled with said sensor means for controlling the flow of waste water in said conduit means.

* * * * *